United States Patent
Lee

(10) Patent No.: US 8,851,750 B2
(45) Date of Patent: Oct. 7, 2014

(54) X-RAY DEVICE

(75) Inventor: Tae-Ho Lee, Yongin (KR)

(73) Assignee: Samsung Display Co., Ltd., Gyeonggi-do (KR)

( * ) Notice: Subject to any disclaimer, the term of this patent is extended or adjusted under 35 U.S.C. 154(b) by 364 days.

(21) Appl. No.: 13/439,653

(22) Filed: Apr. 4, 2012

(65) Prior Publication Data

US 2013/0121476 A1 May 16, 2013

(30) Foreign Application Priority Data

Nov. 15, 2011 (KR) .................. 10-2011-0119122

(51) Int. Cl.
*H01J 31/49* (2006.01)
*A61B 6/00* (2006.01)
*G03B 42/04* (2006.01)
*H02M 1/32* (2007.01)

(52) U.S. Cl.
CPC .............. *G03B 42/04* (2013.01); *A61B 6/4283* (2013.01); *A61B 6/56* (2013.01); *H02M 1/32* (2013.01); *A61B 6/4405* (2013.01)
USPC ........................................................ 378/189

(58) Field of Classification Search
USPC ........................................................ 378/189
See application file for complete search history.

(56) References Cited

U.S. PATENT DOCUMENTS

| | | |
|---|---|---|
| 2009/0190718 A1 | 7/2009 | Fan |
| 2010/0019720 A1 | 1/2010 | Liu et al. |
| 2011/0024644 A1 | 2/2011 | Yoshida et al. |

FOREIGN PATENT DOCUMENTS

| | | |
|---|---|---|
| JP | 2004-020384 A | 1/2004 |
| JP | 2005-148398 A | 6/2005 |
| JP | 2011-30665 A | 2/2011 |
| JP | 2011-045213 A | 3/2011 |

*Primary Examiner* — Jurie Yun
(74) *Attorney, Agent, or Firm* — Knobbe, Martens, Olson & Bear, LLP

(57) ABSTRACT

An X-ray device is disclosed. In one embodiment, the device includes an X-ray detector and a power contactor which includes a contact terminal. The device may further include an X-ray table that provides a space into which the X-ray detector is inserted and that includes a push pin pressing the power contactor, wherein the power contactor selectively protrudes from the inside to the outside of the X-ray detector due to a pressure applied by the push pin, and the contact terminal is electrically connected to a power terminal of the X-ray table. The X-ray detector prevents exposure of the power contactor to the outside thereof when the X-ray detector is carried or transported and thus prevents a malfunction of the X-ray detector.

22 Claims, 8 Drawing Sheets

X-RAY DEVICE

CROSS-REFERENCE TO RELATED PATENT APPLICATION

This application claims the benefit of Korean Patent Application No. 10-2011-0119122, filed on Nov. 15, 2011, in the Korean Intellectual Property Office, the disclosure of which is incorporated herein in its entirety by reference.

BACKGROUND

1. Field

The described technology generally relates to an X-ray device, and more particularly, to an X-ray device in which if needed, a power contactor protrudes from an X-ray detector and is electrically connected to a power terminal.

2. Description of the Related Technology

Typically, an X-ray has a short wavelength and easily passes through a subject. A transmission amount of the X-ray is determined according to the density of the subject. That is, an inner state of the subject may be indirectly identified through a transmission amount of an X-ray that has passed through the subject.

An X-ray device typically includes an X-ray detector. The X-ray detector is a device that detects a transmission amount of the X-ray that has passed through the subject. An inner state of the subject is displayed to the outside on a display device. As an X-ray detector, a flay panel digital radiography (DR) type using DR is widely used. The flay panel DR generally does not use a film.

Typically, an X-ray device may be used as a detector for medical purposes, a non-intrusive inspection apparatus, or the like. In a recent trend, the size or weight of an X-ray device has been reduced, and thus, the X-ray device is easily carried or transported, and even when there is no available power source, the X-ray device is operable by using a secondary battery.

SUMMARY

One inventive aspect is an X-ray device in which if needed, a power contactor protrudes from an X-ray detector due to a pressure applied by a push pin and thus, is electrically connected to a power terminal.

Another aspect is an X-ray device including: an X-ray detector including a power contactor including a contact terminal; and an X-ray table that provides a space into which the X-ray detector is inserted and that includes a push pin pressing the power contactor, wherein the power contactor selectively protrudes from the inside to the outside of the X-ray detector due to a pressure applied by the push pin, and the contact terminal is electrically connected to a power terminal of the X-ray table.

The X-ray detector may have a push pin hole that provides a passage through which the push pin enters the inside of the X-ray detector and a power contactor hole that provides a passage through which the power contactor protrudes from the inside to the outside of the X-ray detector due to a pressure applied by the push pin.

According to an embodiment, the push pin hole is formed in a front surface of the X-ray detector which corresponds to a direction in which the X-ray detector is inserted into the X-ray table and which faces the X-ray table, and the power contactor hole is formed in a side surface of the X-ray detector, which is adjacent to the front surface of the X-ray detector.

According to an embodiment, at least one guide block is attached to the power contactor, at least one guide bar is attached to the guide block, and an elastic bias member is disposed on an outer circumferential surface of the at least one guide bar.

According to an embodiment, the power contactor may have a tapered portion that is to be pressed by the push pin.

According to an embodiment, the tapered portion is formed in such a way that according to a degree of entry of the X-ray detector into the X-ray table, the push pin presses along a slanted surface from a portion of the tapered portion in which the push pin initially contacts the power contactor.

Once the power contactor is exposed to the outside through the power contactor hole, the push pin may be located on a side surface of the power contactor that is opposite to the surface of the power contactor which faces the power contactor hole, so that moving of the power contactor forwards or backwards is prevented.

According to an embodiment, the guide block is attached to a surface of the power contactor, and the guide block has a guide hole through which the guide bar passes.

According to an embodiment, the guide bar is disposed passing through the guide hole in a direction perpendicular to a direction in which the push pin presses the power contactor.

According to an embodiment, an end of the guide bar is fixed on the side surface of the X-ray detector on which the power contactor hole is formed.

According to an embodiment, the elastic bias member may be disposed between an inner wall of the side surface of the X-ray detector and a side surface of the guide block.

According to an embodiment, the guide block is attached to a top or bottom surface of the power contactor, at least one guide bar is formed along a guide hole formed in the guide block on the top or bottom surface of the power contactor, and at least one elastic bias member is formed on an outer circumferential surface of the guide bar.

According to an embodiment, the contact terminal is formed on a protruding surface of the power contactor, and the contact terminal is selectively electrically connected to the power terminal formed inside the X-ray table.

According to an embodiment, the push pin hole and the power contactor hole are formed in a front surface of the X-ray detector which corresponds to a direction in which the X-ray detector is inserted into the X-ray table and which faces the X-ray table.

According to an embodiment, a rotating body is disposed on both sides of the power contactor, the rotating body is rotatably coupled to a hinge axis, and the rotating body is selectively attached to the power contactor in such a way that the power contactor is allowed to move towards the power contactor hole due to a pressure applied by the push pin entering through the push pin hole.

A first elastic bias member that elastically supports the power contactor may be formed on a bottom surface of the power contactor, and an end of the first elastic bias member is fixed on a first fixing portion.

A rotation guide groove may be formed in a bottom surface of the rotating body along a rotation trajectory of the rotating body, and the rotation guide groove is attached to a rotation guide disposed inside the X-ray detector.

According to an embodiment, the rotation guide and the rotation guide groove each have a streamlined shape corresponding to the rotation trajectory of the rotating body.

According to an embodiment, a second elastic bias member is disposed on a side of the rotating body, and an end of the second elastic bias member is fixed on a second fixing portion.

DETAILED DESCRIPTION

Figure 1:
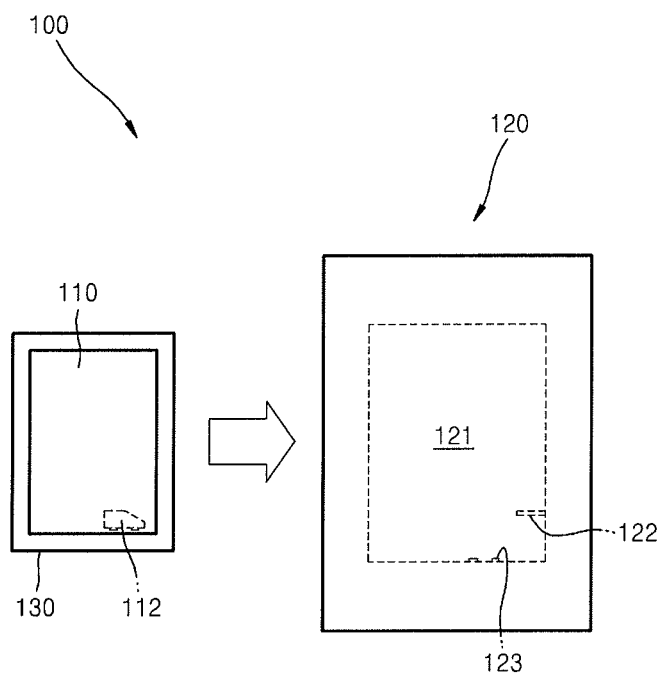
FIG. 1 is a structural view of an X-ray device according to an embodiment.

It will be understood that, although the terms 'first, second, etc.' may be used herein to describe various elements, these elements should not be limited by these terms. These terms are only used to distinguish one element from another.

The terminology used herein is for the purpose of describing particular embodiments only and is not intended to be limiting the disclosed embodiments. As used herein, the singular forms "a," "an," and "the" are intended to include the plural forms as well, unless the context clearly indicates otherwise. It will be further understood that the terms "comprises" and/or "comprising," when used in this specification, specify the presence of stated elements, steps, operations, and/or devices, but do not preclude the presence or addition of one or more other elements, steps, operations, and/or devices.

Expressions such as "at least one of," when preceding a list of elements, modify the entire list of elements and do not modify the individual elements of the list.

Hereinafter, embodiments will be described in detail with reference to the attached drawings in detail. In describing with reference to the drawings, like or corresponding elements are denoted by the same reference numerals and a description thereof will not be repeatedly presented.

FIG. 1 is a structural view of an X-ray device 100 according to an embodiment.

Referring to FIG. 1, the X-ray device 100 includes an X-ray detector 110, an X-ray table 120, and an X-ray incorporated stand 130.

The X-ray detector 110 is disposed on the X-ray incorporated stand 130. The X-ray detector 110 is inserted into an inner space 121 of the X-ray table 120 in a direction indicated by the arrow.

The X-ray detector 110 includes a power contactor 112 for supplying power. The X-ray table 120 contains a push pin 122 that is to contact the power contactor 112 and power terminals 123 that are to be electrically connected to the power contactor 112.

Regarding the X-ray device 100 having such a structure, when the X-ray detector 110 is inserted into the X-ray table 120, the push pin 122 presses the power contactor 112. Due to the pressure of the push pin 122, the power contactor 112 protrudes from the inside to the outside of the X-ray detector 110, and the protruding power contactor 112 electrically connects to the power terminals 123. By doing so, the X-ray device 100 is driven to detect a transmission amount of an X-ray through a subject.

In this regard, the power contactor 112 may selectively protrude from the inside to the outside of the X-ray detector 110 due to a pressure applied by the push pin 122, so that the power contactor 112 is electrically connected to the power terminals 123.

Figure 2:
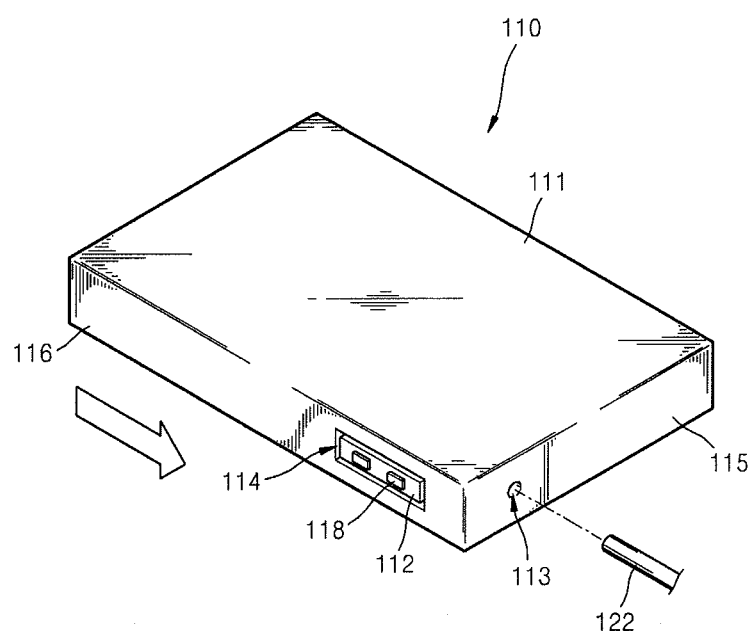
FIG. 2 is a perspective view of the X-ray device of FIG. 1.
Figure 3:
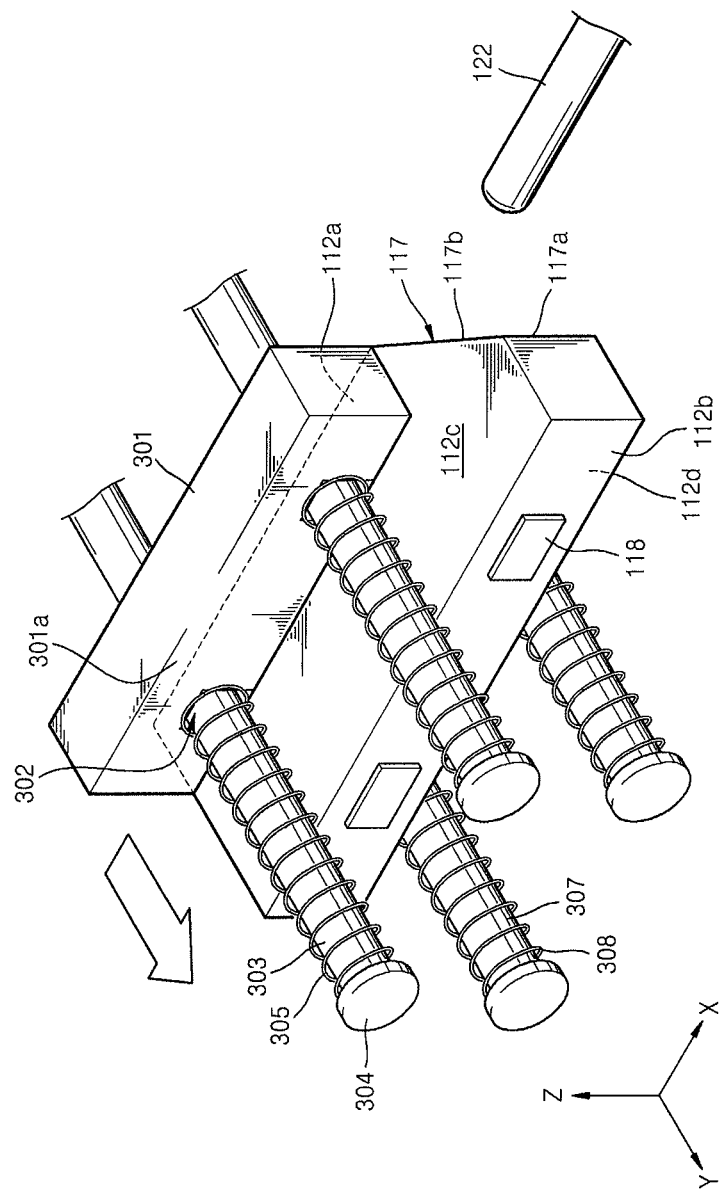
FIG. 3 is a perspective enlarged view of a power contactor illustrated in FIG. 2.
Figure 4:
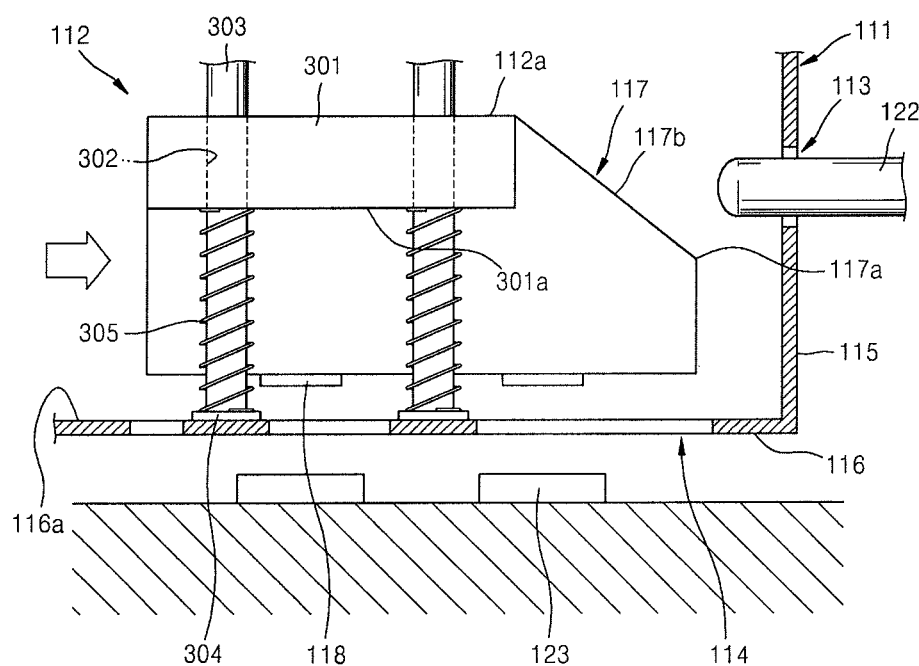
FIG. 4 is a plan cut view of a portion of an X-ray device in which a power contactor illustrated in FIG. 2 is disposed.
Figure 5:
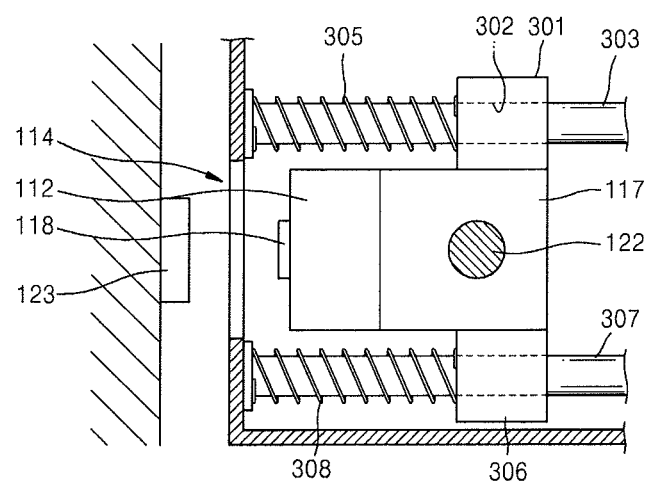
FIG. 5 is a front view of the portion of FIG. 4.

FIG. 2 is a perspective view of the X-ray detector 110 of FIG. 1, FIG. 3 is a perspective enlarged view of the power contactor 112 illustrated in FIG. 2, FIG. 4 is a plan cut view of a portion of the X-ray device 100 in which the power contactor 112 illustrated in FIG. 2 is located, and FIG. 5 is a front cut view of the portion of FIG. 4.

Referring to FIGS. 2 to 5, the X-ray detector 110 includes a main body 111. Inside the main body 111, the power contactor 112 is disposed. The main body 111 has a push pin hole 113 and a power contactor hole 114.

The push pin hole 113 is formed in a front surface 115 of the main body 111, which corresponds to a direction (arrow direction) in which the X-ray detector 110 is inserted into the X-ray table (see 120 of FIG. 1). The push pin hole 113 provides a passage to the push pin 122 disposed inside the X-ray table 120 when the push pin 122 enters the inside of the main body 111.

The power contactor hole 114 is formed in a side surface 116 of the main body 111, which is adjacent to the front surface 115. The power contactor hole 114 provides a passage to the power contactor 112 when the power contactor 112 protrudes from the inside to the outside of the main body 111 due to a pressure applied by the push pin 122.

In this case, the power contactor 112 has a tapered portion 117 that has a tapered shape and is to be pressed by the push pin 122. That is, the tapered portion 117 of the power contactor 112 is formed in such a way that the power contactor 112 is to be slantly pressed according to a degree of the entry of the push pin 122.

When the X-ray detector 110 is inserted into the X-ray table 120, the push pin 122 presses the power contactor 112, moving from a portion 117a of the power contactor 112 which initially contacts the push pin 122 to a slanted surface 117b.

The power contactor 112 pressed by the push pin 122 is moved towards the power contactor hole 114 by a guide member in a direction substantially perpendicular to the pressing direction of the push pin 122, and thus, the power contactor 112 externally protrudes from the main body 111.

Once the power contactor 112 is exposed from the X-ray detector 110 through the power contactor hole 114, to prevent the power contactor 112 from moving forwards and backwards, the push pin 122 is located on a side surface 112a of the power contactor 112. Thus, the push pin 122 continuously presses the power contactor 112. In this regard, the side surface 112a of the power contactor 112 is opposite to an opposite surface 112b of the power contactor 112 which is exposed through the power contactor hole 114.

On the opposite surface 112b of the power contactor 112, a plurality of contact terminals 118 are formed. The contact terminals 118 are electrically connected to the power terminals 123 disposed inside the X-ray table (see 120 of FIG. 1), respectively.

Also, the power contactor 112 externally protrudes from the X-ray detector 110 by a moving member.

To do this, a first guide block 301 is formed in a top surface 112c of the power contactor 112. The first guide block 301 is disposed adjacent to the side surface 112a of the power contactor 112. The first guide block 301 may be integrally formed with the power contactor 112. However, the formation process of the first guide block 301 is not limited thereto. For example, the first guide block 301 is formed by using a separate process and then is attached to the power contactor 112.

The first guide block 301 has a first guide hole 302 in its lower portion. In one embodiment, at least one first guide hole 302 is formed where the first guide block 301 contacts the top surface 112c of the power contactor 112. The first guide hole 302 is formed through the first guide block 301 in a thickness direction of the first guide block 301.

A first guide bar 303 is coupled to the first guide block 301 through the first guide hole 302. The first guide bar 303 is disposed through the first guide hole 302 in a direction (Y direction) which is substantially perpendicular to the direction (X direction) in which the push pin 122 presses the power contactor 112.

In this regard, an end 304 of the first guide bar 303 is fixed on an inner wall 116a of the side surface 116 of the main body 111. The other of the first guide block 301 is fixed on a frame (not shown) placed inside the main body 111.

Because the first guide bar 303 is coupled with the first guide block 301 through the first guide hole 302, when the push pin 122 presses the power contactor 112, the power contactor 112 attached with the first guide block 301 may be moveable along the first guide bar 303 in the Y direction.

In this regard, the first elastic bias member 305 is disposed on an outer circumferential surface of the first guide bar 303. The first elastic bias member 305 is disposed between the inner wall 116a of the side surface 116 of the main body 111 and a side surface 301a of the first guide block 301. The first elastic bias member 305 may be a spring. The first elastic bias member 305 is compressed between the side surface 116 of the main body 111 and the side surface 301a of the first guide block 301 when the first guide block 301 is substantially linearly moved.

Also, on a bottom surface 112d of the power contactor 112, a second guide block 306 (see FIG. 5), a second guide bar 307, and a second elastic bias member 308 may be disposed. The second guide block 306, the second guide bar 307, and the second elastic bias member 308 have substantially the same structures as the first guide block 301, the first guide bar 303, and the first elastic bias member 305, respectively. Thus, the second guide block 306, the second guide bar 307, and the second elastic bias member 308 are not described herein.

Also, the number of first and second guide bars 303 and 307 is not limited as long as they guide the first and second guide blocks 301 and 306.

Also, all of a plurality of the first guide bars 303 and second guide bars 307 need not have the first elastic bias member 305 or the second elastic bias member 308 on their outer circumferential surfaces. That is, some of first or second guide bars 303 and 307 may not have an elastic bias member on their outer circumferential surfaces.

An operation of the X-ray device 100 having such a structure will be described in detail with reference to FIGS. 1 and 2.

The X-ray detector 110 is deposed on the X-ray incorporated stand 130 and then inserted into the inner space 121 of the X-ray table 120. Once the X-ray detector 110 is inserted into the X-ray table 120, the push pin 122 disposed inside the X-ray table 120 is inserted into the X-ray detector 110 through the push pin hole 113 formed in the front surface 115 of the main body 111.

When the push pin 122 is inserted into the X-ray detector 110 through the push pin hole 113, the push pin 122 presses the power contactor 112 disposed inside the main body 111. When the power contactor 112 is pressed in a direction, the power contactor 112 is moved by the moving member and protrudes from the main body 111 through the power contactor hole 114 formed in the side surface 116 of the main body 111.

When the power contactor 112 protrudes towards the outside, the contact terminals 118 of the power contactor 112 are electrically connected to the power terminals 123 of the X-ray table 120, thereby enabling driving of the X-ray detector 110.

Hereinafter, the protruding of the power contactor 112 will be described detail with reference to FIGS. 3 to 9.

First, referring to FIGS. 3 to 5, when the X-ray detector (see 110 of FIG. 1) is inserted into the inner space 121 of the X-ray table 120, the push pin 122 disposed inside the X-ray table 120 enters the inside of the X-ray detector 110 through the push pin hole 113 formed in the front surface 115 of the main body 111 of the X-ray detector 110.

Figure 6:
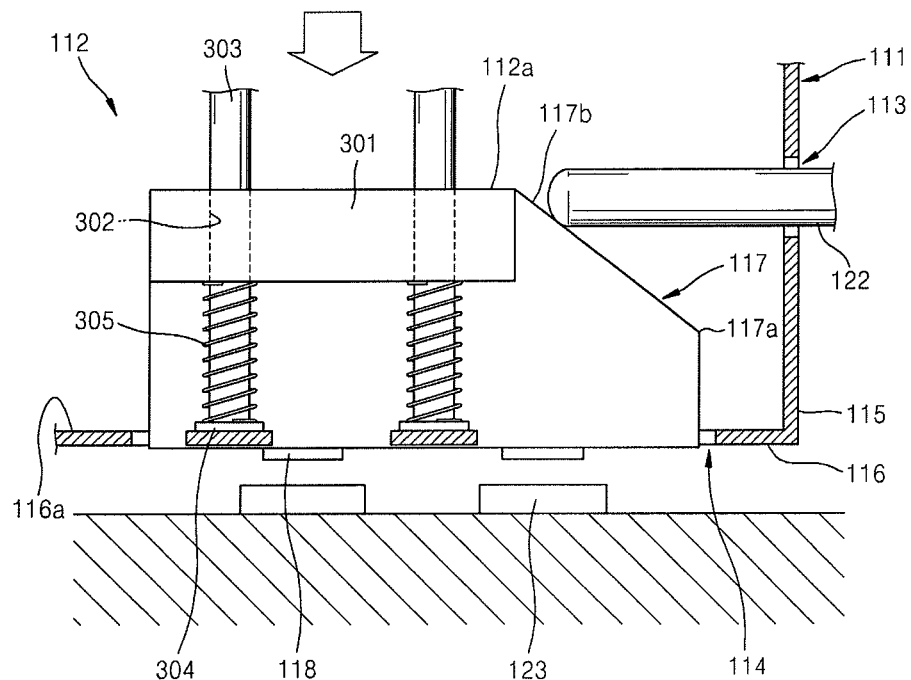
FIG. 6 is a plan view of an X-ray device during a push pin illustrated in FIG. 2 is inserted through a push pin hole.
Figure 7:
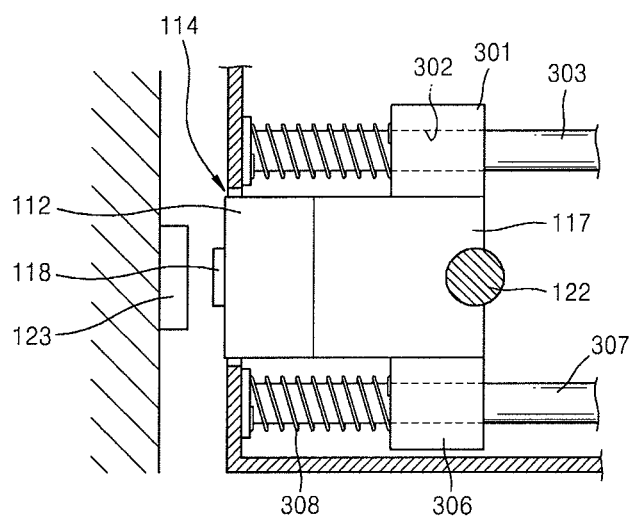
FIG. 7 is a front view of the X-ray device of FIG. 6.

Subsequently, referring to FIGS. 3, 6, and 7, when the push pin 122 is inserted into the main body 111 through the push pin hole 113, an end of the push pin 122 contacts the tapered portion 117 of the power contactor 112.

In this case, when the X-ray detector 110 further enters the X-ray table 120, the push pin 122 is moved along the slanted surface 117b from the portion 117a of the power contactor 112 in which the power contactor 112 initially contacts the push pin 122.

When the push pin 122 is slantly moved along the tapered portion 117 of the power contactor 112 in the X-direction and thus presses the power contactor 112, the first guide block 301 is moved towards the power contactor hole 114 along the first guide bar 303 extending through the first guide hole 302, that is, moved in the Y direction. Accordingly, the power contactor 112 coupled to the first guide block 301 is substantially simultaneously movable at the same time.

In this case, the first elastic bias member 305 is disposed on the outer circumferential surface of the first guide bar 303 between the inner wall 116a of the side surface 116 of the main body 111 and the side surface 301a of the first guide block 301. Accordingly, when the first guide block 301 is moved towards the power contactor hole 114 through the first guide bar 303, the first elastic bias member 305 is compressed between the main body 111 and the first guide block 301.

Also, the second guide block 306 is guided by the second guide bar 307, and the second elastic bias member is compressed when the first elastic bias member 305 is compressed.

Figure 8:
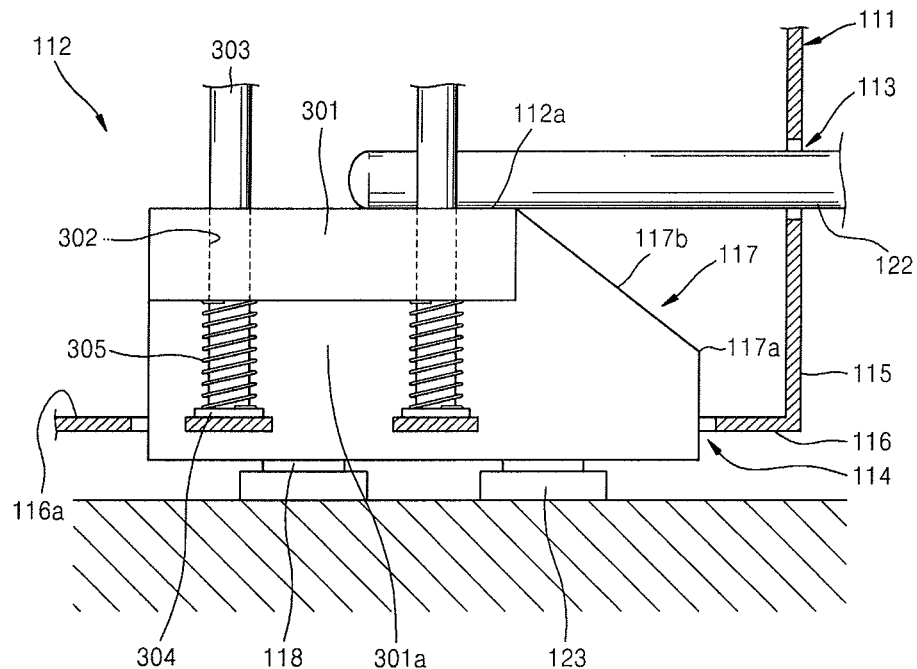
FIG. 8 is a plan view of an X-ray device after a push pin illustrated in FIG. 2 is inserted through a push pin hole.
Figure 9:
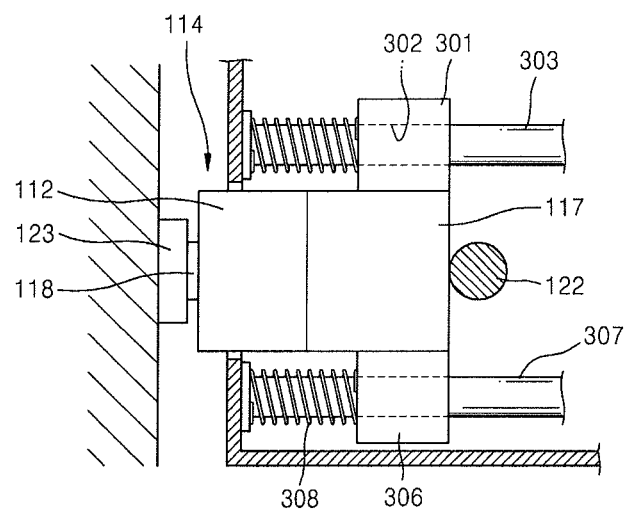
FIG. 9 is a front view of the X-ray device of FIG. 8.

Then, referring to FIGS. 3, 8, and 9, when the power contactor 112 moves towards the power contactor hole 114 due to the pressure applied by the push pin 122, the contact terminals 118 formed on the opposite surface 112b of the power contactor 112 protrude from the main body 111 through the power contactor hole 114 formed in the side surface 116 of the main body 111. The protruding contact terminals 118 are electrically connected to the power terminals 123 disposed inside the X-ray table 120.

Thus, the X-ray device 100 is completely prepared for photographing a subject.

Also, once the push pin 122 ends moving along the slanted surface 117b from the portion 117a of the power contactor 112 in which the power contactor 112 initially contacts the push pin 122, the end of the push pin 112 is located on the side surface 112a of the power contactor 112.

By doing so, when the contact terminals 118 are electrically connected to the power terminals 123, moving of the power contactor 112 in a direction away from the power contactor hole 114 is prevented.

When the push pin 122 is separated from the power contactor 112, due to a restoration force of the elastic bias member 305, the first guide block 301 moves backwards through the first guide bar 303. Thus, the power contactor 112 attached to the first guide block 301 is moved to its original position inside the main body 111, and thus, the contact terminals 118 do not protrude from the main body 111.

Figure 10:
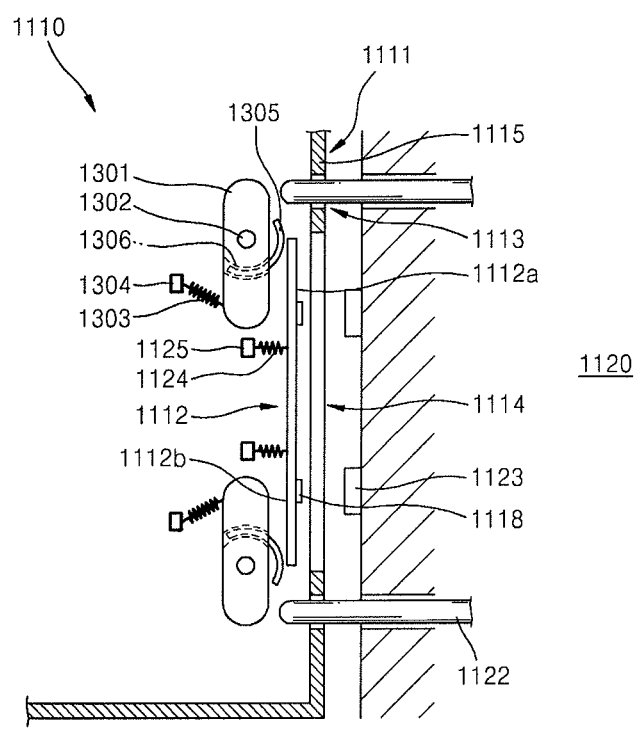
FIG. 10 is a plan view of an X-ray device according to another embodiment when a push pin is entering through a push pin hole.
Figure 11:
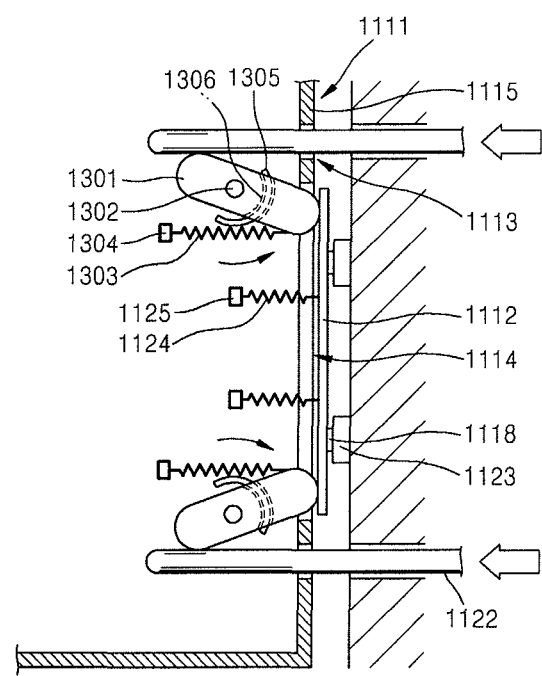
FIG. 11 is a plan view of an X-ray device after the push pin illustrated in FIG. 10 is inserted through a push pin hole.

FIG. 10 is a plan view of an X-ray device when a plurality of push pins 1122 are entering through push pin holes 1113, and FIG. 11 is a plan view of an X-ray device after the push pins 1122 are inserted through push pin holes 1113.

Referring to FIGS. 10 and 11, the X-ray detector 1110 includes a main body 1111. Inside the main body 1111, the power contactor 1112 is disposed. The main body 1111 has push pin holes 1113 and a power contactor hole 1114.

The push pin hole 1113 is formed in a front surface 1115 of the main body 1111 which corresponds to a direction in which the X-ray detector 1110 is inserted into an X-ray table 1120. Inside the X-ray table 1120, the push pins 1122 are disposed. For example, a plurality of push pin holes 1113 may be formed in positions corresponding to the push pins 1122. The push pins 1122 may enter the main body 1111 through the push pin holes 1113 when the X-ray detector 1110 is inserted into the X-ray table 1120.

The power contactor hole 1114 is also formed in the front surface 1115 of the main body 1111. The power contactor hole 1114 may have a size that is sufficient for the power contactor 1112 to pass therethrough when the power contactor 1112 selectively protrudes from the inside to the outside of the main body 1111. The power contactor hole 1112 is formed between the push pins 1122.

A plurality of contact terminals 1118 are formed on a front surface 1112a of the power contactor 1112. When the power contactor 1112 protrudes towards the outside through the power contactor hole 1114 by a moving member, the contact terminals 1118 are electrically connected to power terminals 1123 formed inside the X-ray table 1120.

A first elastic bias member 1124 may be disposed on a bottom surface 1112b of the power contactor 1112. The first elastic bias member 1124 may be attached to a first fixing portion 1125. The first fixing portion 1125 may be fixed on a frame (not shown) of the main body 1111. The first elastic bias member 1124 elastically supports the power contactor 1112 when the power contactor 1112 moves forwards. The first elastic bias member 1124 may be a spring.

A rotating body 1301 may be disposed on both sides of the power contactor 1112. The rotating body 1301 is rotatably coupled to a hinge axis 1302. The rotating body 1301 is rotatable by a predetermined degree according to a pressure applied by the push pins 1122 which are inserted into the main body 1111 through the push pin holes 1113.

A rotation guide 1305 is disposed on a trajectory of the rotating body 1301. That is, a rotation guide groove 1306 is formed in a bottom surface of the rotating body 1301 along a trajectory direction of the rotating body 1301. The rotation guide groove 1306 has a streamlined shape. The rotation guide 1305 formed on the main body 1111 has a shape corresponding to that of the rotation guide groove 1306. The rotation guide 1305 may be inserted into the rotation guide groove 1306. As described above, when the rotating body 1301 rotates, the rotating body 1301 having the rotation guide groove 1306 is rotatable along the rotation guide 1305.

Also, a second elastic bias member 1303 is disposed on a side of the rotating body 1301. The second elastic bias member 1303 is attached to a second fixing portion 1304. The second fixing portion 1304 is attached to a frame (not shown) of the main body 1111. The second elastic bias member 1303 elastically supports the rotating body 1301 when the rotating body 1301 rotates. The second elastic bias member 1303 may be a spring.

An operation of the X-ray device 1100 having such a structure will now be described in detail with reference to FIGS. 10 and 11.

Referring to FIG. 10, the X-ray detector 1110 is inserted into the X-ray table 1120. When the X-ray detector 1110 is inserted into the X-ray table 1120, the push pins 1122 disposed inside the X-ray table 1120 are inserted into the main body 1111 through the push pin holes 1113 formed in the front surface 1115 of the main body 1111

Then, referring to FIG. 11, when the push pins 1122 are inserted into the main body 1111 through the push pin holes 1113, the push pins 1122 rotate the rotating body 1301 disposed inside the main body 1111.

When the rotating body 1301 rotates in a direction, the rotating body 1301 presses the power contactor 1112. The power contactor 1112 protrudes outwardly from the main body 1111 through the power contactor hole 1114 formed in the front surface 1115 of the main body 1111.

When the power contactor 1112 protrudes towards the outside, the contact terminals 1118 formed on the front surface 1112a of the power contactor 1112 are electrically connected to the power terminals 1123 of the X-ray table 1120, thereby enabling driving of the X-ray detector 1110.

The protruding of the power contactor 1112 will now be described in detail.

When the push pins 1122 enter the main body 1111 through the push pin holes 1113, the push pins 1122 contact a side of the rotating body 1301.

When the X-ray detector 1110 further the X-ray table 1120, the rotating body 1301 pressed by the push pins 1122 rotates.

The rotation guide groove 1306 formed in the bottom surface of the rotating body 1301 receives the rotation guide 1305 in such a manner that the rotating body 1301 slides along the rotation guide 1305 when the rotating body 1301 rotates. As such, the rotating body 1301 rotates along the rotation guide 1305.

Due to the rotation of the rotating body 1301, the rotating body 1301 contacts the bottom surface 1112b of the power contactor 1112. The power contactor 1112 that receives the rotational force of the rotating body 1301 moves forwards.

The power contactor 1112 moving towards the X-ray table 1120 protrudes from the main body 1111 through the power contactor hole 1112. When the power contactor 1112 protrudes towards the outside of the main body 1111 through the power contactor hole 1114, the contact terminals 1118 are electrically connected to the power terminals 1123 formed inside the X-ray table 1120.

Thus, the X-ray device 1100 is completely prepared for photographing a subject.

Also, when the pressure applied by the push pins 1122 is removed, the rotating body 1301 is returned to its original location due to a restoration force of the second elastic bias member 1303 fixed on an end of the second fixing portion 1304.

Also, the power contactor 1112 is returned to its original location due to a restoration force of the first elastic bias member 1124 disposed on the bottom surface 1112b of the power contactor 1112.

At least one of the disclosed embodiments provides the following benefits.

First, when the X-ray detector is carried or transported, a power contactor is not exposed to the environment and thus a malfunction of the X-ray detector is minimized or substantially prevented.

Second, shock to the user, which can be caused due to a leakage current from the X-ray detector, is minimized or substantially prevented.

While the above embodiments have been described with reference to the accompanying drawings, it will be understood by those of ordinary skill in the art that various changes in form and details may be made therein without departing from the spirit and scope as defined by the following claims.

What is claimed is:

1. An X-ray device comprising:
   an X-ray detector comprising a power contactor and a contact terminal; and
   an X-ray table configured to receive the X-ray detector, wherein the X-ray table comprises a push pin configured to press the power contactor,
   wherein the power contactor is configured to selectively protrude from an external surface of the X-ray detector based on a pressure applied by the push pin, and
   wherein the contact terminal of the X-ray detector is electrically connectable to a power terminal of the X-ray table.

2. The X-ray device of claim 1, wherein a push pin hole is formed in the X ray detector to receive the push pin of the X-ray table, wherein a power contactor hole is formed in the X ray detector, and wherein the power contactor is configured to protrude from an external surface of the X-ray detector via the power contactor hole.

3. The X-ray device of claim 2, wherein the push pin hole is formed in a front surface of the X-ray detector which corresponds to a direction in which the X-ray detector is inserted into the X-ray table and which faces the X-ray table, and wherein the power contactor hole is formed in a side surface of the X-ray detector, which is adjacent to the front surface of the X-ray detector.

4. The X-ray device of claim 3, wherein at least one guide block is attached to the power contactor, wherein at least one guide bar is attached to the guide block, and wherein an elastic bias member is disposed on an outer circumferential surface of the guide bar.

5. The X-ray device of claim 4, wherein the power contactor has a tapered portion, and wherein the push pin is configured to press the tapered portion.

6. The X-ray device of claim 5, wherein the tapered portion is formed in such a way that according to a degree of entry of the X-ray detector into the X-ray table, the push pin presses along a slanted surface with respect to a portion of the tapered portion in which the push pin initially contacts the power contactor.

7. The X-ray device of claim 6, wherein once the power contactor is exposed from an external surface of the X-ray detector through the power contactor hole, the push pin is located on a side surface of the power contactor that is opposite to the surface of the power contactor which faces the power contactor hole, so as to substantially prevent the forward or backward movement of the power contactor.

8. The X-ray device of claim 4, wherein the guide block is attached to a surface of the power contactor, and wherein the guide block has a guide hole through which the guide bar passes.

9. The X-ray device of claim 8, wherein the guide bar is disposed to pass through the guide hole in a direction substantially perpendicular to a direction in which the push pin presses the power contactor.

10. The X-ray device of claim 9, wherein an end of the guide bar is fixed on the side surface of the X-ray detector on which the power contactor hole is formed.

11. The X-ray device of claim 4, wherein the elastic bias member is disposed between an inner wall of the side surface of the X-ray detector and a side surface of the guide block.

12. The X-ray device of claim 4, wherein the elastic bias member is a spring.

13. The X-ray device of claim 4, wherein the guide block is attached to a top or bottom surface of the power contactor, wherein at least one guide bar is formed along a guide hole formed in the guide block on the top or bottom surface of the power contactor, and wherein at least one elastic bias member is formed on an outer circumferential surface of the guide bar.

14. The X-ray device of claim 2, wherein the push pin hole and the power contactor hole are formed in a front surface of the X-ray detector which corresponds to a direction in which the X-ray detector is inserted into the X-ray table and which faces the X-ray table.

15. The X-ray device of claim 14, wherein a rotating body is disposed on both sides of the power contactor, wherein the rotating body is rotatably coupled to a hinge axis, and wherein the rotating body is selectively attached to the power contactor in such a way that the power contactor moves towards the power contactor hole based on a pressure applied by the push pin.

16. The X-ray device of claim 15, wherein a first elastic bias member that elastically supports the power contactor is formed on a bottom surface of the power contactor, and wherein an end of the first elastic bias member is fixed on a first fixing portion.

17. The X-ray device of claim 16, wherein the first elastic bias member is a spring.

18. The X-ray device of claim 17, wherein a second elastic bias member is disposed on a side of the rotating body, and wherein an end of the second elastic bias member is fixed on a second fixing portion.

19. The X-ray device of claim 18, wherein the second elastic bias member is a spring.

20. The X-ray device of claim 15, wherein a rotation guide groove is formed in a bottom surface of the rotating body along a rotation trajectory of the rotating body, and wherein the rotation guide groove is attached to a rotation guide disposed inside the X-ray detector.

21. The X-ray device of claim 20, wherein the rotation guide and the rotation guide groove each have a streamlined shape corresponding to the rotation trajectory of the rotating body.

22. The X-ray device of claim 1, wherein the contact terminal protrudes from the power contactor, and wherein the contact terminal is selectively electrically connected to the power terminal formed inside the X-ray table.

* * * * *